(12) United States Patent
Nazari et al.

(10) Patent No.: US 7,691,352 B1
(45) Date of Patent: Apr. 6, 2010

(54) PROCESS FOR PREPARATION OF PEROVSKITE

(75) Inventors: Khodadad Nazari, Tehran (IR); Zahra Taheri, Tehran (IR); Naser Seyed Matin, Tehran (IR); Reza Ahmadi, Tehran (IR); Saeed Zarrinpashneh, Tehran (IR); Morteza Rezapour, Tehran (IR)

(73) Assignee: Research Institute of Petroleum Industry (RIPI), Tehran (IR)

( * ) Notice: Subject to any disclaimer, the term of this patent is extended or adjusted under 35 U.S.C. 154(b) by 0 days.

(21) Appl. No.: 12/417,282

(22) Filed: Apr. 2, 2009

Related U.S. Application Data

(60) Provisional application No. 61/117,821, filed on Nov. 25, 2008.

(51) Int. Cl.
*C01F 17/00* (2006.01)
(52) U.S. Cl. .............. 423/263; 423/594.1; 423/594.2; 423/594.3; 423/594.4; 423/594.5; 423/594.6; 423/598; 423/599; 423/594.16; 423/594.9
(58) Field of Classification Search ........... 423/263, 423/594.1, 594.2, 594.3, 594.4, 594.5, 594.6, 423/598, 599, 594.16, 594.9
See application file for complete search history.

(56) References Cited

U.S. PATENT DOCUMENTS 5,200,160 A * 4/1993 Benson et al. .............. 423/235

FOREIGN PATENT DOCUMENTS

EP 1808428 7/2007

OTHER PUBLICATIONS

Zeng et al., "Significant effects of Sintering Temperature on the Performance of La0.6Sr0.4Co0.2Fe0.803-δ Oxygen Selective Membranes." Journal of Membrane Science, 302, 2007, pp. 171-179.
Taheri et al., "Oxygen Permeation and Oxidative Coupling of Methane in Membrane Reactor: a New Facile Synthesis Method for Selective Perovskite Catalyst." Journal of Molecular Catalysis, 286, 2008, pp. 79-86.

* cited by examiner

*Primary Examiner*—Stuart Hendrickson
*Assistant Examiner*—Michelle Hou
(74) *Attorney, Agent, or Firm*—Kenyon & Kenyon LLP

(57) ABSTRACT

A new set of additives to be sued in the preparation of inorganic materials; especially of perovskite nature is proposed. The chemical compositions of the perovskites prepared in the presence of the mentioned additives are found to be more homogenous, leading to better catalytic behavior, including higher selectivity and yields as compared to catalysts of identical formulations prepared through the conventional method of using EDTA/citrate (or other organic additive) method.

19 Claims, 1 Drawing Sheet

1-Steel head
2-Vent
3-Thermocouple
4-Input line
5-Heater (furnace)
6-Perovskite disk membrane
7-Quartz tube
8-Gas Chromatograph
9-$O_2$ cylinder
10-$N_2$ cylinder
11-He cylinder
12-$CH_4$ cylinder

PROCESS FOR PREPARATION OF PEROVSKITE

CROSS REFERENCE TO RELATED APPLICATION

This applications claims priority of U.S. Provisional Patent Application No. 61/117,821, filed on Nov. 25, 2008.

FIELD OF THE INVENTION

The present invention relates to methods used for the preparation of perovskites. The invention more specifically relates to the methods for the preparation of oxygen permeable perovskites with a formula of $ABO_3$, in which A is composed of rare and alkaline earth metal ions and B is a transition metal ion. The invention also relates to the application of such prepared compound as catalyst in different reactions.

BACKGROUND OF THE INVENTION

Nowadays, conversion of methane to more valuable products is of paramount importance, due to the existence of large gas resources throughout the world. Oxidative coupling of methane (OCM) to $C_2$ hydrocarbons (e.g. ethane and ethylene) is a well-known conversion process. The non-selective gas-phase reaction, however, leads to low $C_2$ selectivity and yields.

Several studies have been carried out in packed-bed reactors in co-feed operation mode according to which methane and oxygen were fed to the reactor at the same time. The results, however, were not so promising due to the low $C_2$ selectivity, which was caused by the fact that the oxidant of the process is gaseous molecular oxygen.

To overcome this problem, researchers have tested using perovskite membrane reactors, which have led to the indirect mixing of methane and oxygen during their transport. The major advantage of membrane reactors is preventing the direct mixing of oxygen and methane. This is because the perovskite membrane allows the permeation of ionic oxygen species produced under the operating conditions of the reaction, and keeps methane on the other side. Once the permeated ionic oxygen species reach the methane side, they readily react with the methane that is always in excess amounts due to the transportation mechanism of oxygen. This helps avoid the, side reaction of methane combustion, increasing the selectivity and, to some extent, the yield of the OCM reaction.

Oxygen permeable perovskites that can be used for this purpose are known to have the general formula of $ABO_3$ in which A and B are of rare and alkaline earth metal ions and transition metal ions respectively.

Substitution of alkaline-earth ions on the A-site affects the oxygen nonstoichiometry of the perovskite, while B-site is known to help optimize the catalytic properties of the perovskite-type oxides for oxidation reactions.

Dense membranes of the type of $La_xSr_{1-x}Co_yFe_{1-y}O_{3-\delta}$ are conductors of both oxygen ion and electron.

$La_{0.6}Sr_{0.4}Co_{0.8}Fe_{0.2}O_{3-\delta}$ (LSCF) powders that are commonly used as membrane reactors, are prepared through complexation methods using ethylenediamine tetraacetic acid (EDTA) and an organic acid buffer, which can be later combusted, leaving no traces in the catalyst structure.

According to Pingying Zeng et al (J. of Mem. Sci. 302 (2007)), stoichiometric quantities of the desired metal salts are added to an EDTA, $NH_4OH$ aqueous solution under heating and stirring, and then followed by the addition of citric acid. The pH value of the system is controlled around 6. This is because at lower pH values EDTA precipitates, leading to the formation of non-homogenous $La_{0.6}Sr_{0.4}Co_{0.8}Fe_{0.2}O_{3-\delta}$ powders. The water content of the reaction mixture is then evaporated to yield a dark purple gel, which is then pretreated at 250° C. for several hours to form a solid precursor, which is then calcined at 800° C. for 5 h to obtain the oxide with the desired composition.

The $La_{0.6}Sr_{0.4}Co_{0.8}Fe_{0.2}O_{3-\delta}$ (LSCF) powders prepared through such conventional methods, however, are found to suffer the disadvantage of relatively low $C_2$ hydrocarbon selectivities and yield if used in OCM reactions.

SUMMARY OF THE INVENTION

It is an object of the present invention to develop a complexation method including the application of a group of EDTA derivatives, comprising mono, di, tri, and/or tetra amide products of the amide formation reaction between EDTA and hydrazine, called EDNAD hereinafter.

The preferred compounds of the present invention, called Ethylene Diamine N-Acetyl Diamine (EDNADs) hereinafter, having a formula of:

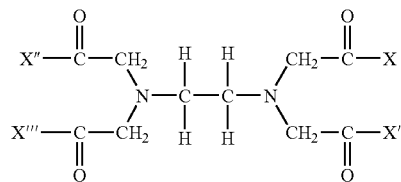

wherein each of X, X', X", X'" is independently selected from the group consisting of $NH-NH_2$, OH, and O, with the proviso that at least one of X, X', X", X'" is $NH-NH_2$ is found to lead to highly homogenized $La_{0.6}Sr_{0.4}Co_{0.8}Fe_{0.2}O_{3-\delta}$ (LSCF) perovskites in a very wide pH range and without the need to add organic buffers, which have excellent catalytic behavior in the oxidative coupling of methane (OCM) reaction.

EDNADs are formed during the amide formation reactions between EDTA and hydrazine and in case all of the X, X', X", X'" branches in the above formula are $NH-NH_2$ the compound is called Ethylene Diamine N, N, N', N', Tetra N-Acetyl Diamine (EDTNAD), which is a preferred compound to be used in the process of the present invention.

According to another embodiment of the present invention the reaction mixture incorporating the EDNADs and the reactants leading to their formation can be directly used in the method of the present invention.

According to another embodiment of the present invention the mixture comprising EDNADs is used as an additive in the production of any other inorganic compound that requires the incorporation of an additive for the dispersion of the active ingredients.

According to a more preferred embodiment of the present invention $La_xSr_{1-x}Co_yFe_{1-y}O_{3-\delta}$ perovskites (LSCF) are prepared through a complexation reaction in the presence of a solution of EDNADs, as additives.

According to another embodiment of the present invention inorganic compounds prepared through the complexation of the ingredients in the presence of EDNADs, enjoy better distribution of the active species throughout their structures (homogeneity) as compared to the EDTA/organic salt method, which can be inferred comparing the turbidity data of the reaction solutions in both cases (example 1 a and b) that is an indicator of the homogeneity of the reaction solutions, finally leading to more homogenous organic compounds.

In the methods of the present invention preparing an inorganic compound, the complexation method provides a reaction of two or more metal ions by dissolving two or more metal salts, preferably soluble metal salts, in an aqueous solution of EDNADs. Preferably the two or more metal salts are selected from the group consisting of salts of Ag, Ba, Sr, Ca, Pb, La, Y, Nb, Ni, Ta, Ir, Ti, Sn, Zr, Mn, Mo, Fe, Cr, Co, and V. Preferably, the metal salts are nitrate salts.

The methods of the present invention preparing an inorganic compound preferably further comprise the steps of heating the obtained compound, evaporating the solution to obtain a material, self-igniting the material, and sintering.

According to another preferred embodiment of the present invention, the reaction mixture comprising the EDNADs does not require buffering agent due to the wide solubility pH range of EDNADs.

According to another embodiment of the present invention the EDNADs solution used for the preparation of the perovskites has a concentration range of about 10 to about 25%, preferably about 15 to about 25% (W/V) with respect to the total amount of EDNADs.

According to another embodiment of the present invention the EDNADs in the solution used for the preparation of the perovskites are composed of a mixture of all mono, di, tri and tetra structural derivatives in a way that the average number of the —NH—NH$_2$ groups in the EDNADs mixture is about 2.0 to about 4.0.

According to a more preferred embodiment of the present invention the average number of the —NH—NH$_2$ groups in the EDNADs mixture is about 3.0 to about 3.9.

According to the most preferred embodiment of the present invention the average number of the —NH—NH$_2$ groups in the EDNADs mixture is about 3.5 about 3.9.

According to another embodiment of the present invention and due to the superior solubility pH range of the EDNADs, and their strong chelating effects as compared to EDTA, there will be no need for the presence of buffers (e.g. organic acids and/or salts like citric and/or citrate) in the reaction solution of the present invention.

According to another embodiment of the present invention stoichiometric amounts of the desired salts are dissolved in an aqueous solution of EDNADs of proper concentration and the obtained solution is heated at about 50 to about 80° C., preferably about 55 to about 70° C., more preferably about 60° C. for about 3 hours while stirring.

According to a more preferred embodiment of the present invention $La_xSr_{1-x}Co_yFe_{1-y}O_{3-\delta}$ perovskites (LSCF) prepared in the presence of EDNADs have very high $C_2$ selectivities (of more than about 70%, preferably more than about 90%, more preferably of about 100%) and OCM reaction yields (of about 3% to about 6%, preferably about 5.0%), which makes them superior over those produced through the conventional EDTA method. The better catalytic performance in this case can also be associated with the more homogenous catalytic structures, prepared through the method of present invention as compared to the EDTA method.

According to another more preferred embodiment of the present invention, in the case of preparing an oxygen permeable OCM-catalytic membrane of $La_xSr_{1-x}Co_yFe_{1-y}O_{3-\delta}$ perovskites (LSCF), stoichiometric amounts of $Sr(NO_3)_2$, $Co(NO_3)_2.6H_2O$, $Fe(NO_3)_3.9H_2O$ and $La(NO_3).6H_2O$ are first dissolved in a about 15 to about 20% (W/V) EDNADs aqueous solution and the obtained solution is heated at about 40 to about 60° C., and most preferably at about 50° C. for about 3 h while stirring.

According to another embodiment of the invention the so-produced $La_{0.6}Sr_{0.4}CO_{0.8}Fe_{0.2}O_{3-\delta}$ perovskite is used as a highly $C_2$ selective catalyst for the oxidative coupling of methane (OCM) reaction.

In one embodiment, the present invention provides a process for preparing a compound that is made by reaction of two or more metal ions comprising dissolving two or more soluble metal salts in a solution that is comprised of the following compound:

$$X''-\underset{O}{\overset{O}{\|}}{C}-CH_2 \quad \underset{/}{\overset{H}{N}}-\underset{|}{\overset{H}{C}}-\underset{|}{\overset{H}{C}}-\underset{\backslash}{N} \quad CH_2-\underset{O}{\overset{O}{\|}}{C}-X$$
$$X'''-\underset{O}{\overset{O}{\|}}{C}-CH_2 \quad H \quad H \quad CH_2-\underset{O}{\overset{O}{\|}}{C}-X'$$

wherein each of X, X', X", X'" is independently selected from the group consisting of NH—NH$_2$, OH, and O, with the proviso that at least one of X, X', X", X'" is NH—NH$_2$ to obtain a solution, and forming a complex by reaction of the metal ions and the above compound with each other in the solution.

In one embodiment the present invention provides a process for preparing a perovskite comprising
 a) combining two or more salts, water and at least a compound of formula:

$$X''-\underset{O}{\overset{O}{\|}}{C}-CH_2 \quad \underset{/}{\overset{H}{N}}-\underset{|}{\overset{H}{C}}-\underset{|}{\overset{H}{C}}-\underset{\backslash}{N} \quad CH_2-\underset{O}{\overset{O}{\|}}{C}-X$$
$$X'''-\underset{O}{\overset{O}{\|}}{C}-CH_2 \quad H \quad H \quad CH_2-\underset{O}{\overset{O}{\|}}{C}-X'$$

wherein each of X, X', X", X'" is independently selected from the group consisting of NH—NH$_2$, OH, and O, with the proviso that at least one of X, X', X", X'" is NH—NH$_2$ to form a solution;
 b) heating the solution to obtain a complex compound of the metal ions and the EDNADs;
 c) evaporating the solvent to obtain a gel-like residue.
 d) heating the gel-like residue in vacuum (pressure of less than about 100 mmHg) (in the absence of $O_2$) to self-ignite, thereby obtaining a powder;
 e) calcining the powder.

In one embodiment the present invention provides an oxygen permeable membrane, comprised of $La_{0.6}Sr_{0.4}Co_{0.8}Fe_{0.2}O_{3-\delta}$, prepared by the above process wherein the membrane when used as a membrane between methane and oxygen for production of $C_2$ products, exhibits a $C_2$ selectivity of about 100% and a yield of about 5% at a temperature of 1073-1173 K.

DETAILED DESCRIPTION OF THE INVENTION

Figure 1:
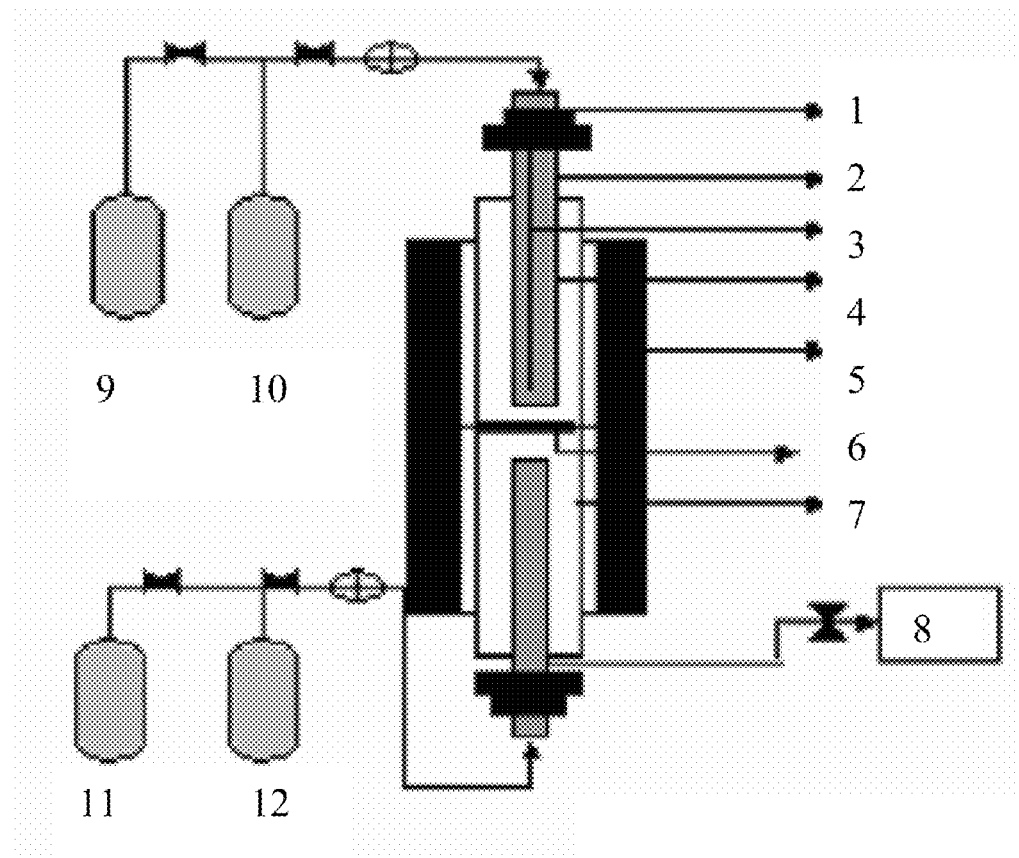
FIG. 1 illustrates a fixed bed reactor using the perovskite membrane of the present invention, used for the comparison experiments.

A new facile complexation procedure in preparation of different perovskites is devised. The advantages of the method, especially in the case of $La_{0.6}Sr_{0.4}Co_{0.8}Fe_{0.2}O_{3-\delta}$ perovskites, are revealed by the modified catalytic behavior of the dense membrane ($La_{0.6}Sr_{0.4}Co_{0.8}Fe_{0.2}O_{3-\delta}$) during the OCM reaction, their pH stability, and also their modified mechanical properties.

According to the embodiments of the present invention the $La_{0.6}Sr_{0.4}Co_{0.8}Fe_{0.2}O_{3-\delta}$ (LSCF) powders, or any other perovskite of desire, are prepared by complexation method using an aqueous solution of EDNADs, where EDNADs refer to compound according to the formula of

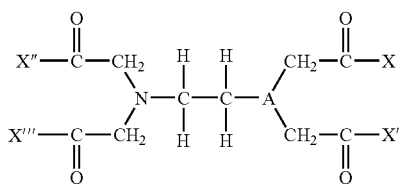

wherein each of X, X', X", X''' is independently selected from the group consisting of $NH-NH_2$, OH, and O, with the proviso that at least one of X, X', X", X''' is $NH-NH_2$. This compound is disclosed in EP 1 808 428, which is incorporated herein by process.

The compounds called Ethylene Diamine N-Acetyl Diamine (EDNADs), are formed during the amidification reactions between EDTA and hydrazine and in case all of the X, X', X", X''' branches in the above formula are $NH-NH_2$ the compound is called Ethylene Diamine N,N, N', N', Tetra N-Acetyl Diamine (EDTNAD) which is a preferred compound to be used in the procedure of the present invention.

In the methods of the present invention preparing a perovskite, the complexation method provides a reaction of two or more metal ions by dissolving two or more metal salts, preferably soluble metal salts, in an aqueous solution of EDNADs. Preferably the two or more metal salts are selected from the group consisting of salts of Ag, Ba, Sr, Ca, Pb, La, Y, Nb, Ni, Ta, Ir, Ti, Sn, Zr, Mn, Mo, Fe, Cr, Co, and V. Preferably, the metal salts are nitrate salts.

The methods of the present invention preparing a perovskite compound preferably further comprise the steps of heating the obtained compound, evaporating the solution to obtain a material, self-igniting the material, and sintering.

According to the invention the best results with respect to the product homogeneity and later catalytic behavior are obtained when average number of the $-NH-NH_2$ groups in the EDNADs mixture is about 2.0 to about 4.0, preferably 3.0 to about 3.9, more preferably about 3.5 to about 3.9, but other mixtures of the compound can be suitably applied for the same purpose.

In the case of using an EDNADs solution for the production of $La_{0.6}Sr_{0.4}Co_{0.8}Fe_{0.2}O_{3-\delta}$ to be used as OCM catalysts, stoichiometric amounts of each salt including $Sr(NO_3)_2$, $Co(NO_3)_2 \cdot 6H_2O$, $Fe(NO_3)_3 \cdot 9H_2O$ and $La(NO_3) \cdot 6H_2O$ are first dissolved in a 10-about 25% (W/V), preferably about 15 to about 25% (W/V), and most preferably about 18% (W/V) aqueous EDNADs solution. It is noteworthy that the minimum amount concentration of the EDNADs in the solutions should constitute a 1:1 stoichiometric ratio between the total metal ions and the EDNADs, but any excess amount of EDNADs can also be used, since it will not interfere with the modified membrane properties and will burn in the self-ignition step. The obtained solution is then heated at about 50 to about 80° C., preferably about 55 to about 70° C. and most preferably about 60° C. for about 3 h while stirring.

The obtained gel-like dark-red material obtained after evaporating the solution at room temperature is then self-ignited at about 200° C. in a vacuum oven. Preferably, evaporating the solution is carried out at about 50° C. to about 60° C. under vacuum (at a pressure of less than about 100 mm Hg). The step of self-igniting preferably comprises heating to a temperature of about 120° C. to about 250° C., more preferably at about 150° C. to about 230° C., even more preferably at about 200° C. Preferably, the step of self-igniting is carried out in vacuum, at a pressure of less than 100 mm Hg. Then, the obtained gray powder is calcinated at about 950° C. to about 1200° C. for 5 h. The obtained black oxide powder is pressed into disk pellets under 400-600 MPa (4000-6000 bar) hydraulic pressure. Disks are sintered at about 1200° C. for 10 hours by heating and then cooling rate at 2° C./min. Both sides of the sintered membrane are then polished with about 1000 mesh SiC paper to give a final thickness of approximately 0.7-1.0 mm. The catalysts are then used in an OCM setup to check their catalytic effects during the oxidative coupling of methane (OCM) reaction. (See Journal of Molecular Catalysis A: Chemical 286 (2008) 79-86, incorporated herein by reference in its entirety).

It is also noteworthy that the solution of EDNADs as an additive can be extended to the production of other inorganic compounds that are produced through complexation methods.

The oxygen permeable membrane of the present invention comprised of $La_{0.6}Sr_{0.4}Co_{0.8}Fe_{0.2}O_{3-\delta}$ prepared as described above, has high selectivity and provides a high yield. Preferably the membrane when used as a membrane between methane and oxygen for production of $C_2$ products, exhibits a $C_2$ selectivity of more than about 70% and a yield of about 3% to about 6% at a temperature of 1073-1173K. More preferably the selectivity is more than about 90%, even more preferably about 100%, and the yield is about 5%.

EXAMPLES

The below examples are meant to elaborate on the subject-matter of the current invention, but the scope of the invention is not limited to the examples at all.

Example 1

In order to indicate the higher potential of EDNAD as a proper chelating reagent for the production of perovskites, two experiments are conducted for comparing the homogeneity and pH-stability of the metal complexes prepared though the EDNAD and EDTA methods.

a—EDTA/Citrate Method 8.068 gr of $H_4$-EDTA (ethylene diamine tetra acetic acid) was dissolved in an ammonia solution (8.0 M). The initial pH of the solution is adjusted at about 8. Then stoichiometric amounts of metallic nitrates $Sr(NO_3)_2$, $La(NO_3)_3 \cdot 6H_2O$, $Co(NO_3)_2 \cdot 6H_2O$ and $Fe(NO_3)_3 \cdot 9H_2O$ were added, respectively so that the molar ratio of EDTA to total metal cation content was 1.5:1.0. After addition of the second salt, some coagulated materials formed in the solution. Indeed after addition of the metal salts, pH of the solution decreases considerably (becomes acidic). By heating and addition of excess amounts of ammonia solution coagulates dissolved. The same problem was faced with the addition of $3^{rd}$ and $4^{th}$ salts, in which small size particles were formed in the solution.

Again, using heat and extra amounts of ammonia solution the problem was solved. These findings indicate that the complexes between the metal ions and EDTA do not show high stability with the changes in pH of the solution and the solution is not really homogeneous probably because of partial formation of metallic hydroxides at alkaline pHs and the insolubility of EDTA salts in acidic pH values. To check the homogeneity of the solution at high pH values, turbidity of the solutions at pH 8.0 and pH 12.0 were measured using a Hach laboratory turbidimeter. The results are summarized in table 1.

Turbidity of the solutions was obtained 95 and 57 NTU (Nephelometric Turbidity Units), respectively. At pH 3.0 the solution contained large amounts of coagulates and precipitates, which makes it not useable for the production of any homogenous organic structures.

b—EDNADs Method

A solution of metal ions/EDNADs with a molar ratio of EDNAD to total metal cation content of 1.5:1.0 was prepared. Using the EDNADs chelating agent solution none of the above problems were observed. The solution was clear and homogeneous at acidic and alkaline media. For example turbidity of the complex solutions of metal ions/EDNAD at pH 3.0, pH 8.0 and pH 12.0 were obtained 4, 2 and 1 NTU, respectively. The results are summarized in table 1.

Comparing the results of the experiments in the table shows that the products of the EDNADs have a much higher homogeneity due to the more homogenous reaction media, which has no turbidity as compared to the EDTA method that has relatively higher turbidity values.

TABLE 1

Comparison of the turbidity (and hence homogeneity) of the EDTA and EDNADs reaction solutions at different pH values

| EDTA method | | EDNADs method | |
| --- | --- | --- | --- |
| pH | Turbidity (NTU) | pH | Turbidity (NTU) |
| 3 | Insoluble | 3 | 4 |
| 8 | 95 | 8 | 2 |
| 12 | 57 | 12 | 1 |

Also after three days the EDTA solutions were even more turbid, while the EDNADs solutions were totally transparent, which is another indication of the homogeneity of perovskite-preparation metal complex solutions in the presence of EDNADs.

Example 2

Preparation of a Perovskite OCM Catalyst Using EDNADs 3 gr of a $La_{0.6}Sr_{0.4}Co_{0.8}Fe_{0.2}O_{3-\delta}$ perovskite OCM catalyst was prepared through the EDNAD method as describe below:

To an 18% W/V solution of EDNADs having an average —NH—NH$_2$ content of 3.5-3.9 (which was prepared by diluting the 70% W/V solution) were added 1.1415 gr of Sr(NO$_3$)$_2$, 3.5037 gr of La(NO$_3$)$_3$.6H$_2$O, 3.2046 gr of Co(NO$_3$)$_2$.6H$_2$O and 1.1007 gr of Fe(NO$_3$)$_3$.9H$_2$O respectively, with a 30 minute interval before the addition of each salt. The resulting dark-red solution was evaporated to form a gel, which was further dried and oxidized in a vacuum oven in 200° C. The resulting powder was calcinated for 5 hours in 950° C. with a heating rate of 2° C./min. The obtained black oxide powder is pressed into disk pellets under 400 MPa (4000 bar) hydraulic pressure. Disks were sintered at 1200° C. for 10 h by heating and then cooling rate at 2° C./min. Both sides of the sintered membrane are then polished with 1000 mesh SiC paper to give a final thickness of approximately 0.7-1.0 mm. The catalysts are then used in an OCM setup to check their catalytic effects during the oxidative coupling of methane (OCM) reaction.

Example 3

Preparation of a Perovskite OCM Catalyst Using the EDTA/Citrate 3 gr of a $La_{0.6}Sr_{0.4}Cu_{0.8}Fe_{0.2}O_{3-\delta}$ perovskite OCM catalyst was prepared through the EDNAD method as describe below:

To a solution containing 12.0514 gr EDTA, 36.0854 gr NH$_4$OH, and 84.4285 gr of deionized water, having a pH of 8-9 were added 1.1415 gr of Sr(NO$_3$)$_2$, 3.5037 gr of La(NO$_3$)$_3$.6 H$_2$O, 3.2046 gr of Co(NO$_3$)$_2$.6H$_2$O and 1.1007 gr of Fe(NO$_3$)$_3$.9H$_2$O respectively, with a 30 minute interval before the addition of each salt, and the final pH was fixed at 6-6.5 using nitric acid and/or ammonia solutions. Then the pH was adjusted at 6.0 using citric acid (8.6222 gr). The resulting dark-red solution was evaporated to form a gel, which was further dried and oxidized in a vacuum oven in 200° C. The resulting powder was calcinated for 5 hours in 950° C. with a heating rate of 2° C./min. The obtained black oxide powder is pressed into disk pellets under 400 MPa (4000 bar) hydraulic pressure. Disks were sintered at 1200° C. for 10 h by heating and then cooling rate at 2° C./min. Both sides of the sintered membrane are then polished with 1000 mesh SiC paper to give a final thickness of approximately 0.7-1.0 mm. The catalysts are then used in an OCM setup to check their catalytic effects during the oxidative coupling of methane (OCM) reaction.

Example 4

Reactor Tests of the Two Catalysts

OCM reactions were carried out in the LSCF dense membrane reactors prepared according to examples 2 and 3 according to Scheme 1.

In both cases a mixture of He and CH$_4$ was fed on one side and oxygen on the other side. Experimental results obtained from the membrane reactor were compared for two procedures of LSCF preparation. Experimental conditions and catalyst characteristics are shown in Tables 2.

For LSCF membrane catalyst prepared by both EDTA/Citrate and EDNADs methods, the best results including C$_2$ selectivity, conversion and yield were obtained at a temperature range of 1023-1173 K. Below 1023 K the extent of oxygen permeation is low and above 1240 K the sealing of membrane reactor was lost, hence the values of C$_2$ selectivity is only reported for the above optimum temperature range. A maximum methane conversion of 5.01% was obtained for the membrane reactor prepared through the EDNADs method.

$$YeildC_2 = Conversion\ CH_4 \times S_{C_2}$$

Where $S_{C_2}$ is the selectivity of the reaction towards the C$_2$ product, over the catalyst. It must be mentioned that in the OCM reaction the low conversion is not a limiting factor, instead, the higher C$_2$ selectivity is of paramount importance because in contrast to the fixed-bed catalyst, the membrane catalyst showed no methane combustion (CO$_x$ formation reactions).

$C_2$ selectivity, as the most important parameter for OCM reaction, for the LSCF dense membrane prepared through the EDNADs method was found to be about 100% over the used temperature range of 1073-1153 K.

$$\text{Selectivity}_{C_2} = \frac{2(C_2H_4 + C_2H_6)}{[CO + CO_2 + 2(C_2H_6 + C_2H_6)]} \times 100$$

The results obtained for the catalyst prepared through the EDTA/citrate method are also given in table 2. As it is clear, the catalyst prepared through the method of the present invention is superior to the EDTA/citrate catalyst with respect to selectivity and yield.

TABLE 2

Reactor test results for the catalysts prepared through the conventional EDTA method and the method of the present invention

| Membrane (EDNADs-method) | | Membrane (EDTA-method) | |
| --- | --- | --- | --- |
| x | 0.6, 0.8 | x | 0.6 0.8 |
| y | 0.6, 0.8 | y | 0.6, 0.8 |
| Preferable δ range | 0.00-0.15 | Preferable δ range | 0.00-0.18 |
| Most preferable δ | 0.00 | Most Preferable δ | 0.15 |
| Preferable Temp. range (K) | 1023-1173 | Preferable Temp. range (K) | 1023-1173 |
| Most preferable Temp (K) | 1073-1153 | Most Preferable Temp (K) | 1123 |
| $O_2$ partial pressure | 0.1-1.0 bar | $O_2$ partial pressure | 0.1-1.0 bar |
| Thickness | 0.5-1.0 mm | Thickness | 0.5-1.0 mm |
| $C_2$ sel. % | 100 | $C_2$ sel. % | 52.33 |
| Yield % | 5.01 | Yield % | 2.26 |

Catalyst formula: $A_{1-x}A'_xB_{1-y}B'_yO_{3-\delta}$ (A:La; A':Sr; B:Co, B':Fe)

What is claimed it:

1. A process for preparing a compound that is made by reaction of two or more metal ions comprising dissolving two or more soluble metal salts in a solution that is comprised of the following compound:

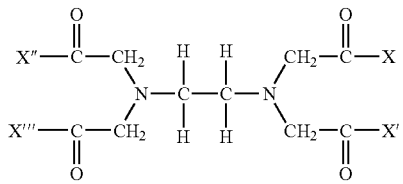

wherein each of X, X', X", X'" is independently selected from the group consisting of NH—$NH_2$, OH, and O, with the proviso that at least one of X, X', X", X'" is NH—$NH_2$ to obtain a solution, and forming a complex by reaction of the metal ions and the above compound with each other in the solution.

2. The process of claim 1, wherein the metals are selected from the group consisting of Ag, Ba, Sr, Ca, Pb, La, Y, Nb, Ni, Ta, Ir, Ti, Sn, Zr, Mn, Mo, Fe, Cr, Co, and V.

3. The process of claim 1, wherein the soluble metal salts are nitrate salts.

4. The process of claim 3, wherein the salts are two or more of $Sr(NO_3)_2$, $Co(NO_3)_2 \cdot 6H_2O$, $Fe(NO_3)_3 \cdot 9H_2O$ and $La(NO_3) \cdot 6H_2O$.

5. A process for preparing a compound with a perovskite structure from the product of the process of claim 1, comprising further heating the product, evaporating, self igniting, and calcining.

6. The process in claim 1, wherein the process is used to obtain $La_{0.6}Sr_{0.4}Co_{0.8}Fe_{0.2}O_{3-\delta}$ (LSCF) powders.

7. The process of claim 1, wherein the solution is an aqueous solution and comprises two or more different substitutions for X, X', X", X'".

8. The process of claim 1, wherein a mixture of the compound is used having an average number of NH—$NH_2$ of about 2.0 to about 4.0.

9. The process of claim 1, wherein a mixture of the compound is used having an average number of NH—$NH_2$ of about 3.0 to about 3.9.

10. The process of claim 1, wherein a mixture of the compound is used having an average number of NH—$NH_2$ of about 3.5 to about 3.9.

11. The process of claim 1, wherein the concentration range of the EDNADs in the solution is between a 1:1 stoichiometric ratio of the EDNADs and the dissolved metal ions to any excess amount.

12. The process of claim 1, wherein the solution has a concentration range of about 10 to about 25% (W/V) with respect to the EDNADs.

13. The process of claim 1, wherein the solution has a concentration range of about 15 to about 25% (W/V) with respect to the EDNADs.

14. The process of claim 1, wherein the solution has a concentration range of about 18% (W/V) with respect to the EDNADs.

15. The process of claim 1, wherein the solution does not have a pH buffering agent.

16. A process for preparing a perovskite comprising
a) combining two or more salts, water and at least a compound of formula:

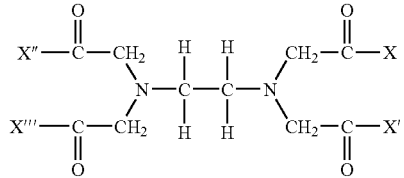

wherein each of X, X', X", X'" is independently selected from the group consisting of NH—$NH_2$, OH, and O, with the proviso that at least one of X, X', X", X'" is NH—$NH_2$ to form a solution;
b) heating the solution to obtain a complex compound of the metal ions and the EDNADs;
c) evaporating the solvent to obtain a gel-like residue;
d) heating the gel-like residue in vacuum (pressure of less than about 100 mmHg) (in the absence of $O_2$) to self-ignite, thereby obtaining a powder;
e) calcining the powder.

17. The process of claim 16, wherein the process is carried out with step b) at a temperature of about 50° C. to about 80° C., step c) at about 50° C. to about 60° C. under vacuum (pressure of less than about 100 mmHg), step d) at about 120 to about 250° C., and step e) at about 950° C. to about 1200° C.

18. A process for preparing an oxygen permeable disk membrane comprising pressing the powder of claim 16 and sintering the pressed powder.

19. The process of claim 18, wherein the pressing is carried out at pressure of about 4000 to about 6000 bar.

* * * * *